(12) United States Patent
Nie et al.

(10) Patent No.: US 11,911,037 B2
(45) Date of Patent: Feb. 27, 2024

(54) MEDICAL DEVICE, STAPLER, AND ROTARY LOCKING MECHANISM

(71) Applicant: EZISURG MEDICAL CO. LTD., Shanghai (CN)

(72) Inventors: Hong Lin Nie, Shanghai (CN); Xiao Jian Zhang, Shanghai (CN)

(73) Assignee: EZISURG MEDICAL CO. LTD., Shanghai (CN)

( * ) Notice: Subject to any disclaimer, the term of this patent is extended or adjusted under 35 U.S.C. 154(b) by 289 days.

(21) Appl. No.: 17/610,011

(22) PCT Filed: May 8, 2020

(86) PCT No.: PCT/CN2020/089156
§ 371 (c)(1),
(2) Date: Nov. 9, 2021

(87) PCT Pub. No.: WO2020/228601
PCT Pub. Date: Nov. 19, 2020

(65) Prior Publication Data
US 2022/0192669 A1 Jun. 23, 2022

(30) Foreign Application Priority Data
May 10, 2019 (CN) .......................... 201910392558.1

(51) Int. Cl.
*A61B 17/00* (2006.01)
*A61B 17/115* (2006.01)

(52) U.S. Cl.
CPC ..... *A61B 17/115* (2013.01); *A61B 2017/0046* (2013.01); *A61B 2017/00477* (2013.01)

(58) Field of Classification Search
CPC .................................................. A61B 17/00
See application file for complete search history.

(56) References Cited

U.S. PATENT DOCUMENTS

| | | | |
|---|---|---|---|
| 2006/0079912 | A1 | 4/2006 | Whitfield et al. |
| 2016/0242757 | A1* | 8/2016 | Cryder ................... A61B 17/02 |
| 2022/0133317 | A1* | 5/2022 | Von Stein ........ A61B 17/07207 |
| | | | 227/175.1 |

FOREIGN PATENT DOCUMENTS

| | | |
|---|---|---|
| CN | 101507641 A | 8/2009 |
| CN | 202437265 U | 9/2012 |

(Continued)

OTHER PUBLICATIONS

International Search Report and Written Opinion in corresponding International Application No. PCT/CN2020/089156 dated Aug. 5, 2020 (13 pages).

*Primary Examiner* — Praachi M Pathak
(74) *Attorney, Agent, or Firm* — Venable LLP (57) ABSTRACT

A medical device, a stapler, and a rotation locking mechanism, the medical device including a handheld mechanism, a connecting mechanism, and an actuator. The connecting mechanism is connected to the handheld mechanism and the actuator. The handheld mechanism is internally provided with a first rotation locking mechanism and a first transmission mechanism connected to the first rotation locking mechanism. A second rotation locking mechanism matching the first rotation locking mechanism is disposed on the connecting mechanism. When the first transmission mechanism is in a first state, the first rotation locking mechanism and the second rotation locking mechanism are in an unlocked state, such that the connecting mechanism is rotatable. When the first transmission mechanism is in a second state, the first rotation locking mechanism and the second rotation locking mechanism are in a locked state, such that the connecting mechanism is locked, thereby improving surgery safety and surgery efficiency.

15 Claims, 5 Drawing Sheets

(56) References Cited

FOREIGN PATENT DOCUMENTS

| CN | 104739476 A | 7/2015 |
|---|---|---|
| CN | 106470620 A | 3/2017 |
| CN | 208031243 U | 11/2018 |

* cited by examiner

MEDICAL DEVICE, STAPLER, AND ROTARY LOCKING MECHANISM

CROSS-REFERENCE TO RELATED APPLICATIONS

This application is a U.S. National Stage application of PCT/CN2020/089156, filed May 8, 2020 and published on Nov. 19, 2020 as WO 2020/228601, which claims the benefit of Chinese Patent Application No. 201910392558.1 filed on May 10, 2019, all of which are hereby incorporated by reference in their entireties.

TECHNICAL FIELD

The present invention belongs to the technical field of medical devices, relates to a medical device, and more particularly to a stapler and a rotation locking mechanism.

BACKGROUND

With the development of science and technology, some medical devices present, such as a stapler. A handle of the stapler needs to be used in cooperation with an adapter and an actuator; the adapter can rotate freely in a firing axis direction, so as to drive the actuator to rotate synchronously. Using the rotatable adapter, a user can more easily and accurately control the actuator to reach a site to be operated.

In some existing staplers, the rotation of the adapter cannot be locked. During a surgery, due to an external force applied to the stapler by a tissue or a mistaken touch of the user on an adapter dial, the adapter and actuator will rotate unexpectedly, thereby affecting the surgery safety and the anastomosis quality to a certain extent. Alternatively, the actuator needs to be re-controlled, thereby affecting the surgery efficiency.

The other existing staplers, which are provided with an adapter rotation locking mechanism, all need to trigger the locking manually, thereby requiring an additional operation. Furthermore, the rotation of the adapter may be locked unexpectedly due to misoperation, and the adapter needs to be unlocked by means of a reset operation, Thereby affecting user experience and the surgery efficiency.

In view of the existing status, a novel medical device is urgent to be designed to overcome the above defects of the existing medical devices.

SUMMARY

The present invention provides a medical device, a stapler, and a rotation locking mechanism, and can ensure the surgery safety and improve the surgery efficiency.

In order to solve the above technical problem, according to one aspect of the present invention, the following technical solution is adopted:

A medical device, including: a handheld mechanism, a connecting mechanism, and an actuator, wherein the connecting mechanism is respectively connected to the handheld mechanism and the actuator;

the handheld mechanism is internally provided with a first transmission mechanism and a first rotation locking mechanism; the first transmission mechanism is connected to the first rotation locking mechanism; a second rotation locking mechanism matching the first rotation locking mechanism is disposed on the connecting mechanism;

when the first transmission mechanism is in a first state, the first rotation locking mechanism and the second rotation locking mechanism are in an unlocked state, such that the connecting mechanism is in a rotatable state; and when the first transmission mechanism is in a second state, the first rotation locking mechanism and the second rotation locking mechanism are in a locked state, such that the connecting mechanism is in a locked state.

As one embodiment of the present invention, when the first transmission mechanism is in the first state, the first rotation locking mechanism is not engaged with the second rotation locking mechanism; and when the first transmission mechanism is in the second state, the first rotation locking mechanism is engaged with the second rotation locking mechanism.

As one embodiment of the present invention, the first rotation locking mechanism includes a rotation locking slider and a first elastic mechanism; the rotation locking slider comprises a first part of the slider, a second part of the slider, and a third part of the slider;

the first elastic mechanism and the second part of the slider are cooperatively disposed; when the second part of the slider is under the action of a force in a first direction, the first elastic mechanism generates an elastic deformation;

the first part of the slider and the first transmission mechanism are cooperatively disposed; when the first transmission mechanism is in the first state, the first part of the slider bears a first thrust force in the first direction applied by the first transmission mechanism, such that the entire rotation locking slider is under the action of the first thrust force, and the first elastic mechanism generates an elastic deformation; the rotation locking slider is located at a first position; the third part of the slider and the second rotation locking mechanism are in an unlocked state;

when the first transmission mechanism is in the second state, the first elastic mechanism resets, and the rotation locking slider is located at a second position, such that the third part of the slider and the second rotation locking mechanism are in a locked state.

As one embodiment of the present invention, the first transmission mechanism is provided with a first step; and all or some of the first part of the slider cooperates with the first step.

As one embodiment of the present invention, the handheld mechanism includes a first bump; one end of the first elastic mechanism is disposed on the first bump, and the other end is connected to the second part of the slider.

As one embodiment of the present invention, the handheld mechanism is provided with a first guide structure; and a part of the rotation locking slider is located in the first guide structure, such that the rotation locking slider slides in a predetermined space under the limit of the first guide structure and the first transmission mechanism.

As one embodiment of the present invention, the first elastic mechanism is a spring.

As one embodiment of the present invention, the medical device further includes a driving mechanism, wherein the driving mechanism is connected to the first transmission mechanism, and can drive the first transmission mechanism to move.

As one embodiment of the present invention, the second rotation locking mechanism comprises a series of tooth structures; when the first rotation locking mechanism is engaged with the tooth structures, the first rotation locking mechanism and the second rotation locking mechanism are in the locked state.

According to another aspect of the present invention, the following technical solution is adopted: a stapler, including a handle, an adapter, and an actuator, wherein one end of the adapter is connected to the handle, and the other end is connected to the actuator;

the handle is internally provided with a first transmission mechanism and a first rotation locking mechanism; the first transmission mechanism is connected to the first rotation locking mechanism; a second rotation locking mechanism is disposed on the adapter;

when the first transmission mechanism is in a first state, the first rotation locking mechanism is not engaged with the second rotation locking mechanism, such that the adapter is in a rotatable state; and when the first transmission mechanism is in a second state, the first rotation locking mechanism is engaged with the second rotation locking mechanism, such that the adapter is in a locked state.

According to another aspect of the present invention, the following technical solution is adopted: a rotation locking mechanism, including a first transmission mechanism, a first rotation locking mechanism, and a second rotation locking mechanism, wherein the first transmission mechanism is connected to the first rotation locking mechanism; the second rotation locking mechanism matching the first rotation locking mechanism is disposed on a connecting mechanism;

when the first transmission mechanism is in a first state, the first rotation locking mechanism and the second rotation locking mechanism are in an unlocked state, such that the connecting mechanism is in a rotatable state; and when the first transmission mechanism is in a second state, the first rotation locking mechanism and the second rotation locking mechanism are in a locked state, such that the connecting mechanism is in a locked state.

The present invention has the following beneficial effects: the medical device, the stapler, and the rotation locking mechanism provided by the present invention can ensure the surgery safety and improve the surgery efficiency.

In the medical device such as the stapler provided by the present invention, the mechanism can be automatically locked by rotating the adapter; once a relative position of the actuator and a tissue is determined, before and after the stapler starts to close and fire a staple, the rotation of the adapter can be automatically locked; from such time to the time the anastomosis is completed, the adapter does not rotate any more, thereby ensuring the ideal cutting and anastomosis position of the actuator clamp and the tissue.

The present invention can avoid the unexpected rotation due to an external force applied to the stapler by a tissue or a mistaken touch of the user on an adapter dial, thereby ensuring the surgery safety, and improving the surgery efficiency and the anastomosis quality to a certain extent. Furthermore, the user only needs to perform an anastomosis surgery in a normal flow without performing an additional operation or paying attention to the execution of the rotation locking mechanism.

DETAILED DESCRIPTION OF THE EMBODIMENTS

The preferred embodiments of the present invention will be described in detail hereafter with reference to the accompanying drawings.

In order to further understand the present invention, the preferred implementation solutions of the present invention will be described hereafter in combination with the embodiments. However, it should be understood that the descriptions are only intended to further describe the features and advantages of the present invention, but not to limit the claims of the present invention.

The following descriptions are provided on the basis of a few typical embodiments, and the present invention is not only limited to the scope described by the embodiments. Mutual substitutions of the same or similar means in the prior art with the technical features in the embodiments are also in the protection scope of the present invention.

The present invention discloses a medical device, the medical device including a handheld mechanism, a connecting mechanism, and an actuator, wherein the connecting mechanism is respectively connected to the handheld mechanism and the actuator; the handheld mechanism is internally provided with a first transmission mechanism and a first rotation locking mechanism; the first transmission mechanism is connected to the first rotation locking mechanism; a second rotation locking mechanism matching the first rotation locking mechanism is disposed on the connecting mechanism; when the first transmission mechanism is in a first state, the first rotation locking mechanism and the second rotation locking mechanism are in an unlocked state, such that the connecting mechanism is in a rotatable state; and when the first transmission mechanism is in a second state, the first rotation locking mechanism and the second rotation locking mechanism are in a locked state, such that the connecting mechanism is in a locked state.

In one embodiment of the present invention, that the first transmission mechanism is in a first state refers to that the medical device is in an unlocked (the actuator does not execute an action) state; and that the first transmission mechanism is in a second state refers to that the medical device is in a locked (the actuator executes an action) state.

In one embodiment of the present invention, when the first transmission mechanism is in the first state, the first rotation locking mechanism is not engaged with the second rotation locking mechanism; and when the first transmission mechanism is in the second state, the first rotation locking mechanism is engaged with the second rotation locking mechanism.

Figure 1:
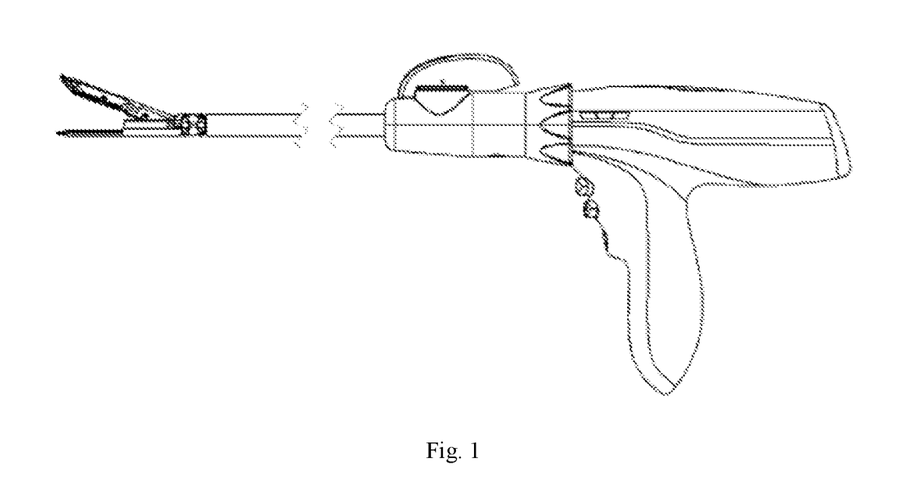
FIG. 1 is an overall structural schematic view of a stapler according to one embodiment of the present invention.
Figure 2:
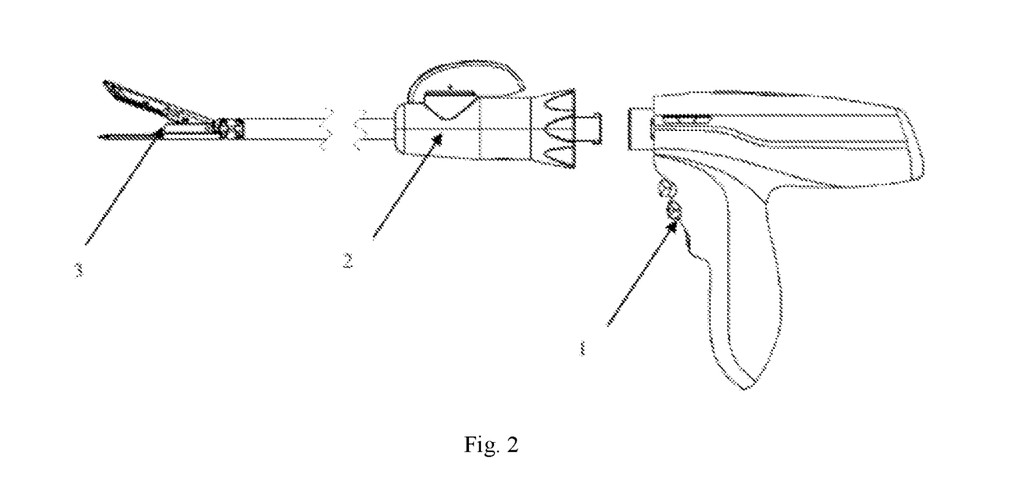
FIG. 2 is a structural schematic view of an adapter and a handle which are separated according to one embodiment of the present invention.

In one embodiment of the present invention, the medical device is a stapler; certainly, the medical device can also be other medical devices in addition to the stapler. FIG. 1 is an overall structural schematic view of a stapler according to one embodiment of the present invention; and FIG. 2 is a structural schematic view of an adapter and a handle which are separated according to one embodiment of the present invention. With reference to FIG. 1-2, the stapler includes a handle 1, an adapter 2, and an actuator 3. The rotation locking mechanisms can lock the rotation of the adapter.

In one embodiment of the present invention, the adapter 2 is inserted into the handle 1 at a fixed angle; after being mounted in place, the adapter 2 can rotate freely in the firing axis direction; after the relative position of the actuator and the surgery site is determined, a handle button can control the actuator clamp to close and squeeze the tissue. Once the driving motor rotates and the actuator clamp starts to close, the rotation locking mechanism automatically becomes effective; and from such time to the time the anastomosis is completed, the adapter 2 does not rotate any more.

Figure 3:
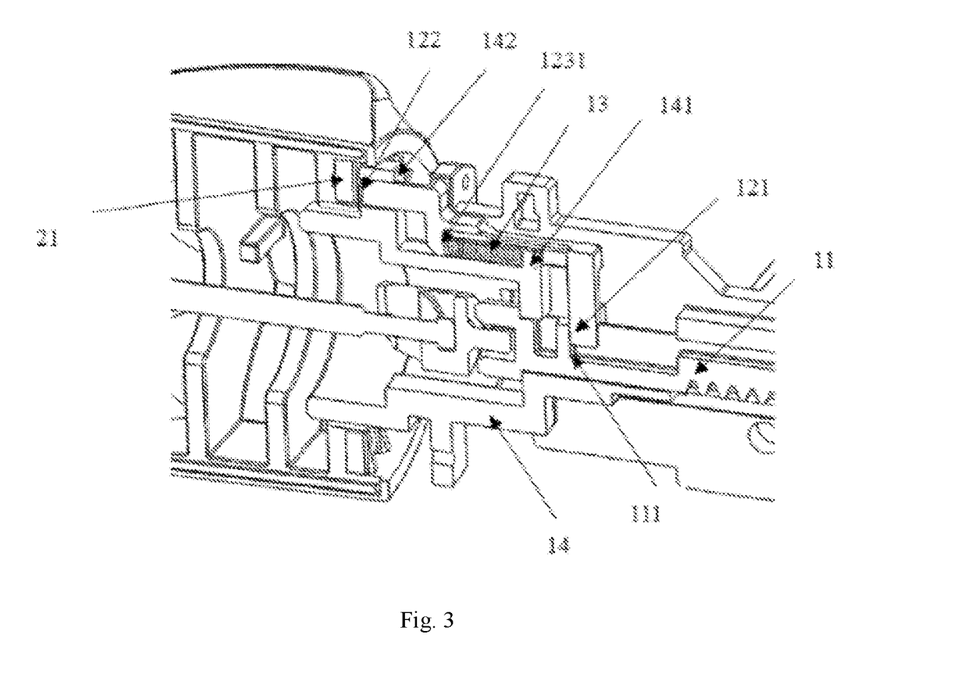
FIG. 3 is a structural schematic view of a rotation locking mechanism in the handle according to one embodiment of the present invention.
Figure 4:
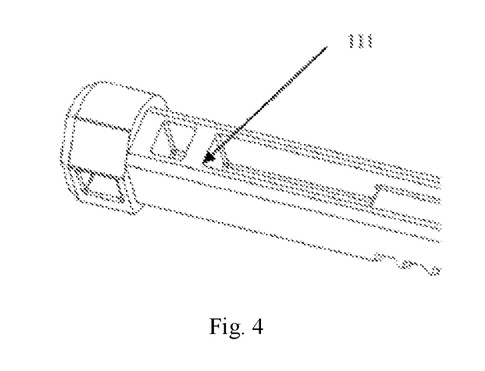
FIG. 4 is a structural schematic view of a rack groove according to one embodiment of the present invention.
Figure 5:
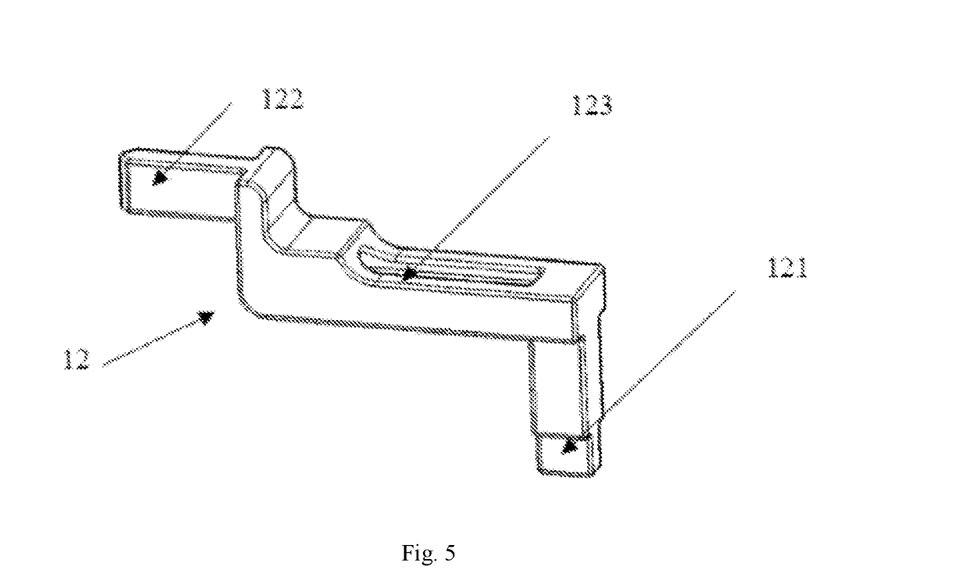
FIG. 5 is a structural schematic view of a rotation locking slider according to one embodiment of the present invention.

In one embodiment of the present invention, the rotation locking mechanism of the medical device (for example, the stapler) includes a rack 11, a rotation locking slider 12, a compressed spring 13, a handle frame 14, and a series of tooth structures 21, as shown in FIG. 3-5.

FIG. 5 is a structural schematic view of a rotation locking slider according to one embodiment of the present invention; With reference to FIG. 5, in one embodiment of the present invention, the first rotation locking mechanism includes a rotation locking slider 12 and a first elastic mechanism 13; the rotation locking slider 12 includes a first part of the slider (a bottom of the slider) 121, a second part of the slider (an intermediate portion of the slider) 123, and a third part of the slider (a top of the slider) 122.

Figure 6:
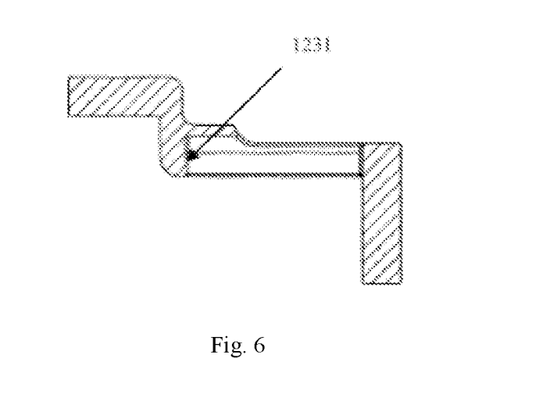
FIG. 6 is a sectional view of the rotation locking slider according to one embodiment of the present invention.

FIG. 6 is a sectional view of the rotation locking slider according to one embodiment of the present invention; With reference to FIG. 6, in one embodiment of the present invention, the third part of the slider 123 is provided with a left wall 1231 structure, wherein the position of the left wall 1231 can see FIG. 3.

In one embodiment of the present invention, the first transmission mechanism is a rack 11, as shown in FIG. 3. FIG. 4 is a structural schematic view of a rack step according to one embodiment of the present invention. With reference to FIG. 4, in one embodiment of the present invention, the rack 11 is provided with a first step 111. All or some of the first part of the slider 121 cooperates with the first step 111.

In one embodiment of the present invention, the medical device further includes a driving mechanism (for example, a driving motor), wherein the driving mechanism is connected to the first transmission mechanism, and can drive the first transmission mechanism to move.

Figure 8:
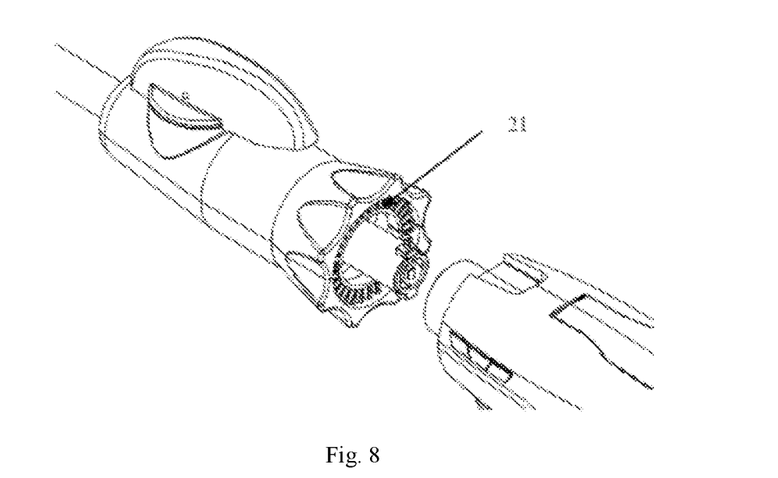
FIG. 8 is a structural schematic view of a tooth structure on an end surface of the adapter according to one embodiment of the present invention.

FIG. 8 is a structural schematic view of a tooth structure on an end surface of the adapter according to one embodiment of the present invention. With reference to FIG. 3, in one embodiment of the present invention, the second rotation locking mechanism includes a series of tooth structures 21, wherein the tooth structures 21 are located at an opening of the adapter 2; and the tooth structures 21 are provided with uniformly distributed protruding structures. When the third part of the slider 122 in the first rotation locking mechanism is engaged with any one protruding tooth of the tooth structures 21, the first rotation locking mechanism and the tooth structures 21 can be locked.

FIG. 3 is a structural schematic view of a rotation locking mechanism in the handle according to one embodiment of the present invention; With reference to FIG. 3, in one embodiment of the present invention, the first elastic mechanism 13 and the second part of the slider 123 are cooperatively disposed; when the second part of the slider 123 is under the action of a force in a first direction (for example, in the handle direction), the first elastic mechanism 13 generates an elastic deformation (for example, the first elastic mechanism is compressed). In one embodiment of the present invention, the first elastic mechanism 13 is a spring. In another embodiment of the present invention, the first elastic mechanism 13 can also be a tension spring.

The first part of the slider 121 and the first transmission mechanism (the rack 11) are cooperatively disposed; when the first transmission mechanism (the rack 11) is in the first state, the first part of the slider 121 bears a first thrust force in the first direction applied by the first transmission mechanism (the rack 11) (in one embodiment of the present invention, the first direction is the direction towards the handle), such that the entire rotation locking slider 12 is under the action of the first thrust force, and the first elastic mechanism 13 generates an elastic deformation (is compressed); the rotation locking slider 12 is located at a first position at which position the third part of the slider 122 and the tooth structure 21 are in an unlocked state.

When the first transmission mechanism (the rack 11) is in the second state, the first elastic mechanism 13 resets (the reset direction is opposite to the first direction, for example, the direction away from the handle); and the rotation locking slider 12 is located at a second position at which position the third part of the slider 122 and the tooth structure 21 are in a locked state.

Figure 7:
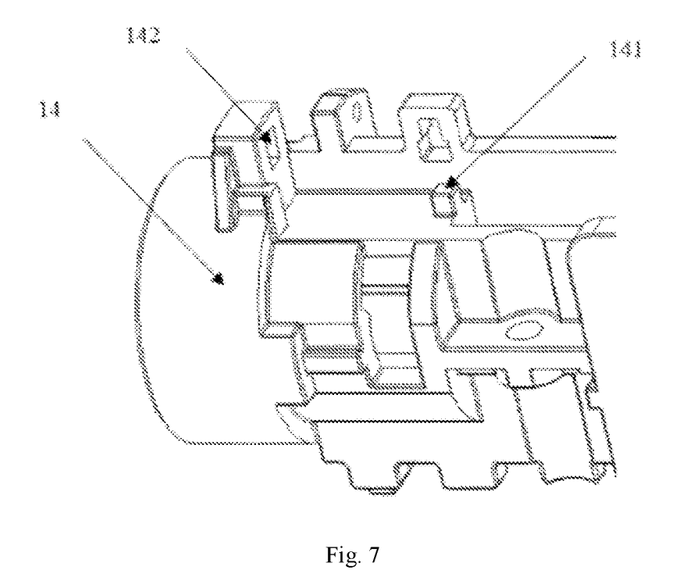
FIG. 7 is a structural schematic view of a handle frame bump according to one embodiment of the present invention.

In one embodiment of the present invention, the handheld mechanism is provided with a first guide structure; and a part of the rotation locking slider is located in the first guide structure, such that the rotation locking slider slides in a predetermined space under the limit of the first guide structure and the first transmission mechanism. FIG. 7 is a structural schematic view of a handle frame bump according to one embodiment of the present invention. With reference to FIG. 7, in one embodiment of the present invention, the handle frame 14 is provided with a bump 141 structure and a first guide structure 142. The first part of the slider 121 is disposed in the rack step 111, and the third part of the slider 122 penetrates through the first guide structure 142 of the handle frame 14. A proximal end of the first elastic mechanism 13 (the compressed spring) presses against the bump 141 of the handle frame 14, and a distal end presses against the left wall 1231 of the second part of the slider 123 (the intermediate portion of the slider), as shown in FIG. 3.

During use of the product, the rotation locking mechanism is linked to the motor driven rack 11; the user only needs to perform an anastomosis surgery in a normal flow without performing an additional operation or paying attention to the execution of the rotation locking mechanism.

Only when the rack 11 is at the origin (that is, the clamp completely opens) and the system is in an initial state, the rack step 111 limits the first part of the slider 121; the rotation locking slider 12 slides to the proximal end; the second part of the slider 123 compresses the first elastic mechanism 13 (the compressed spring); the third part of the slider 122 is separated from the tooth structure 21, and the adapter 2 can rotate freely.

Figure 9:
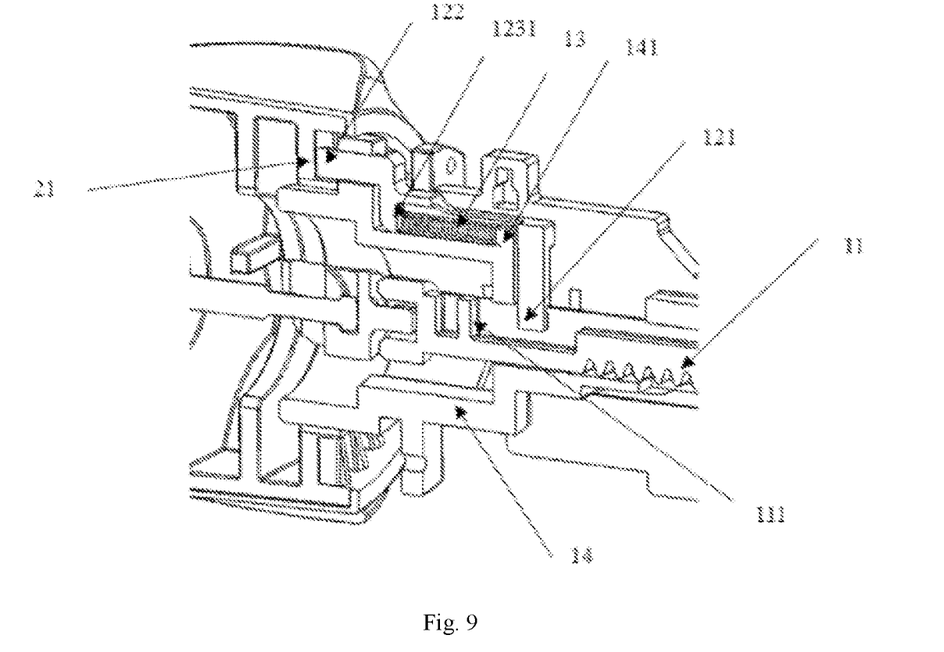
FIG. 9 is a structural schematic view when a rotation locking function becomes effective according to one embodiment of the present invention.
Figure 10:
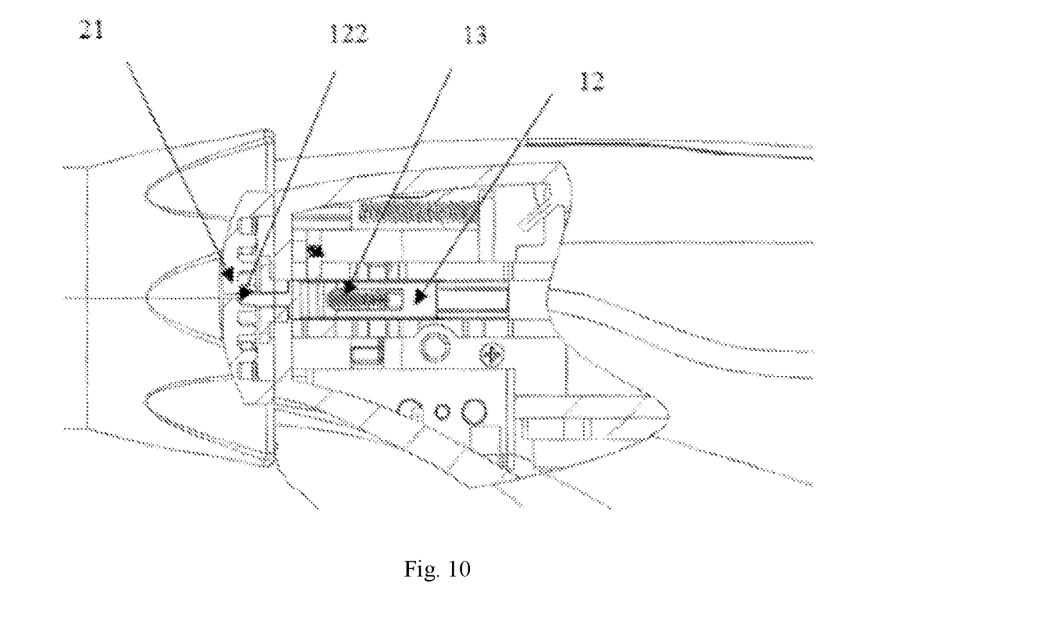
FIG. 10 is a vertical sectional view when the rotation locking function becomes effective according to one embodiment of the present invention.

When the rack moves forwards and the actuator clamp starts to close and enter a firing state, the rack step 111 releases the first part of the slider 121; the second part of the slider 123 is pushed out by the first elastic mechanism 13 (the compressed spring) connected thereto; the third part of the slider 122 is engaged with any one of the tooth structures 21 on the end surface of the adapter, so as to realize a locking action, as shown in FIGS. 9 and 10. Afterwards, unless the system manually enters a reset state again or the system enters the reset state after the anastomosis is completed, under other situations, the rotation can be reliably locked by means of the rotation locking slider 12, the first elastic mechanism 13 (the compressed spring), and the tooth structures 21.

During use of the product, if the actuator clamp only closes but does not enter the firing state, the handle button can be operated to reset the stapler to the origin, or can be reset by means of pulling back with a hand; when the rack 11 returns to the initial position, the rack step 111 limits the first part of the slider 121 (the bottom of the slider), such that the rotation locking slider 12 slides to the proximal end, and the third part of the slider 122 (the top of the slider) is separated from the tooth structure 21, as shown in FIG. 3. In this case, the rotation locking mechanism is automatically released, and restores to the initial state to rotate the adapter 2; and the relative position of the actuator clamp and the tissue is re-determined to re-start the normal surgery flow.

The present invention further discloses a rotation locking mechanism, the rotation locking mechanism including a first transmission mechanism, a first rotation locking mechanism, and a second rotation locking mechanism, wherein the first transmission mechanism is connected to the first rotation locking mechanism; the second rotation locking mechanism matching the first rotation locking mechanism is disposed on a connecting mechanism; when the first transmission mechanism is in a first state, the first rotation locking mechanism and the second rotation locking mechanism are in an unlocked state, such that the connecting mechanism is in a rotatable state; and when the first transmission mechanism is in a second state, the first rotation locking mechanism and the second rotation locking mechanism are in a locked state, such that the connecting mechanism is in a locked state.

In one embodiment of the present invention, the rotation locking mechanism adopts the structure as described in the above embodiment. The first transmission mechanism is a rack 11; the first rotation locking mechanism includes a rotation locking slider 12 and a first elastic mechanism 13; and the second rotation locking mechanism is a tooth structure 21.

In the present invention, the adapter is inserted into the handle at a fixed angle; after being mounted in place, the adapter can rotate freely in the firing axis direction; after the relative position of the actuator clamp and the surgery site is determined, the handle button can control the clamp to close and squeeze the tissue. Once the driving motor rotates and the clamp starts to close, the rotation locking mechanism automatically becomes effective; and from such time to the time the anastomosis is completed, the adapter does not rotate any more.

During use of the product, the rotation locking mechanism is linked to the motor driven rack; the user only needs to perform an anastomosis surgery in a normal flow without performing an additional operation or paying attention to the execution of the rotation locking mechanism. Only when the rack is at the origin (that is, the clamp completely opens) and the system is in an initial state, the rack step limits the rotation locking slider, and the adapter can rotate freely. When the rack moves forwards and the clamp starts to close and enter the firing state, the rack releases the rotation locking slider; the rotation locking slider is pushed out by the compressed spring connected thereto; the top of the slider is engaged with any one of the tooth structures on the end surface of the adapter, so as to realize a locking action. Afterwards, unless the system manually enters a reset state again or the system enters the reset state after the anastomosis is completed, under other situations, the rotation can be reliably locked by means of the rotation locking slider, the compressed spring, and the tooth structures.

During use of the product, if the clamp only closes but does not enter the firing state, the handle button can be operated to reset the stapler to the origin; when the rack returns to the initial position, the rack step limits the rotation locking slider, and the rotation locking slider is separated from the tooth structure. In this case, the rotation locking mechanism is automatically released, and restores to the initial state to rotate the adapter; and the relative position of the actuator clamp and the tissue is re-determined to re-start the normal surgery flow.

In summary, the present invention has the following beneficial effects: the medical device, the stapler, and the rotation locking mechanism provided by the present invention can ensure the surgery safety and improve the surgery efficiency.

In the medical device such as the stapler provided by the present invention, the mechanism can be automatically locked by rotating the adapter; once a relative position of the actuator clamp and a tissue is determined, before and after the stapler starts to close and fire a staple, the rotation of the adapter can be automatically locked; from such time to the time the anastomosis is completed, the adapter does not rotate any more, thereby ensuring the ideal cutting and anastomosis position of the actuator clamp and the tissue.

The present invention can avoid the unexpected rotation due to an external force applied to the stapler by a tissue or a mistaken touch of the user on an adapter dial, thereby ensuring the surgery safety, and improving the surgery efficiency and the anastomosis quality to a certain extent. Furthermore, the user only needs to perform an anastomosis surgery in a normal flow without performing an additional operation or paying attention to the execution of the rotation locking mechanism.

The technical features of the above embodiments can be combined at will. In order to enable the descriptions to be concise, all the possible combinations of the technical features in the above embodiments are not described. However, the combinations of the technical features, as long as the combinations do not conflict, should be all concluded in the scope recorded in the description.

The above descriptions and applications of the present invention are descriptive, but not intended to limit the scope of the present invention in the above embodiments. The variations and changes of the embodiments disclosed herein are possible, and various substitutions and equivalent components of the embodiments are commonly known for a person skilled in the art. A person skilled in the art should understand that the present invention can be implemented in other forms, structures, arrangements, proportions, and other assemblies, materials, and components without departing from the spirit or essential features of the present invention. The embodiments disclosed herein may have other variations and changes without departing from the scope and spirit of the present invention.

The invention claimed is:

1. A medical device, comprising a handheld mechanism, a connecting mechanism, and an actuator, wherein the connecting mechanism is respectively connected to the handheld mechanism and the actuator;

the handheld mechanism is internally provided with a first transmission mechanism and a first rotation locking mechanism; the first transmission mechanism is connected to the first rotation locking mechanism; a second rotation locking mechanism matching the first rotation locking mechanism is disposed on the connecting mechanism;

when the first transmission mechanism is in a first state, the first rotation locking mechanism and the second rotation locking mechanism are in an unlocked state, such that the connecting mechanism is in a rotatable state; and when the first transmission mechanism is in a second state, the first rotation locking mechanism and the second rotation locking mechanism are in a locked state, such that the connecting mechanism is in a locked state.

2. The medical device according to claim 1, wherein when the first transmission mechanism is in the first state, the first rotation locking mechanism is not engaged with the second rotation locking mechanism; and when the first transmission mechanism is in the second state, the first rotation locking mechanism is engaged with the second rotation locking mechanism.

3. The medical device according to claim 1, wherein the first rotation locking mechanism comprises a rotation locking slider and a first elastic mechanism; the rotation locking slider comprises a first part of the slider, a second part of the slider, and a third part of the slider; the first elastic mechanism and the second part of the slider are cooperatively disposed; when the second part of the slider is under the action of a force in a first direction, the first elastic mechanism generates an elastic deformation;

the first part of the slider and the first transmission mechanism are cooperatively disposed;

when the first transmission mechanism is in the first state, the first part of the slider bears a first thrust force in the first direction applied by the first transmission mechanism, such that the entire rotation locking slider is under the action of the first thrust force, and the first elastic mechanism generates an elastic deformation; the rotation locking slider is located at a first position; the third part of the slider and the second rotation locking mechanism are in an unlocked state; and when the first transmission mechanism is in the second state, the first elastic mechanism resets, and the rotation locking slider is located at a second position, such that the third part of the slider and the second rotation locking mechanism are in a locked state.

4. The medical device according to claim 3, wherein the first transmission mechanism is provided with a first step; and all or some of the first part of the slider cooperates with the first step.

5. The medical device according to claim 3, wherein the handheld mechanism comprises a first bump; one end of the first elastic mechanism is disposed on the first bump, and the other end is connected to the second part of the slider.

6. The medical device according to claim 3, wherein the handheld mechanism is provided with a first guide structure; and a part of the rotation locking slider is located in the first guide structure, such that the rotation locking slider slides in a predetermined space under the limit of the first guide structure and the first transmission mechanism.

7. The medical device according to claim 3, wherein the first elastic mechanism is a spring.

8. The medical device according to claim 1, wherein the medical device further comprises a driving mechanism; and the driving mechanism is connected to the first transmission mechanism, and is configured to drive the first transmission mechanism to move.

9. The medical device according to claim 1, wherein the second rotation locking mechanism comprises a series of tooth structures; when the first rotation locking mechanism is engaged with the tooth structures, the first rotation locking mechanism and the second rotation locking mechanism are in the locked state.

10. A stapler, comprising a handle, an adapter, and an actuator, wherein one end of the adapter is connected to the handle, and the other end is connected to the actuator;

the handle is internally provided with a first transmission mechanism and a first rotation locking mechanism; the first transmission mechanism is connected to the first rotation locking mechanism; a second rotation locking mechanism is disposed on the adapter;

when the first transmission mechanism is in a first state, the first rotation locking mechanism is not engaged with the second rotation locking mechanism, such that the adapter is in a rotatable state; and when the first transmission mechanism is in a second state, the first rotation locking mechanism is engaged with the second rotation locking mechanism, such that the adapter is in a locked state.

11. A rotation locking mechanism, comprising a first transmission mechanism, a first rotation locking mechanism, and a second rotation locking mechanism, wherein the first transmission mechanism is connected to the first rotation locking mechanism; the second rotation locking mechanism matching the first rotation locking mechanism is disposed on a connecting mechanism;

when the first transmission mechanism is in a first state, the first rotation locking mechanism and the second rotation locking mechanism are in an unlocked state, such that the connecting mechanism is in a rotatable state; and when the first transmission mechanism is in a second state, the first rotation locking mechanism and the second rotation locking mechanism are in a locked state, such that the connecting mechanism is in a locked state.

12. The rotation locking mechanism according to claim 11, wherein the first rotation locking mechanism comprises a rotation locking slider and a first elastic mechanism; the rotation locking slider comprises a first part of the slider, a second part of the slider, and a third part of the slider;

the first elastic mechanism and the second part of the slider are cooperatively disposed; when the second part of the slider is under the action of a force in a first direction, the first elastic mechanism generates an elastic deformation;

the first part of the slider and the first transmission mechanism are cooperatively disposed; when the first transmission mechanism is in the first state, the first part of the slider bears a first thrust force in the first direction applied by the first transmission mechanism, such that the entire rotation locking slider is under the action of the first thrust force, and the first elastic mechanism generates an elastic deformation; the rotation locking slider is located at a first position; the third part of the slider and the second rotation locking mechanism are in an unlocked state; and when the first transmission mechanism is in the second state, the first elastic mechanism resets, and the rotation locking slider is located at a second position, such that the third part of the slider and the second rotation locking mechanism are in a locked state.

13. The rotation locking mechanism according to claim 12, wherein
the first transmission mechanism is provided with a first step; and all or some of the first part of the slider cooperates with the first step.

14. The rotation locking mechanism according to claim 12, wherein
the rotation locking mechanism comprises a first bump; one end of the first elastic mechanism is disposed on the first bump, and the other end is connected to the second part of the slider.

15. The rotation locking mechanism according to claim 12, wherein
the rotation locking mechanism is provided with a first guide structure; and a part of the rotation locking slider is located in the first guide structure, such that the rotation locking slider slides in a predetermined space under the limit of the first guide structure and the first transmission mechanism.

* * * * *